United States Patent
Lidor-Hadas et al.

(10) Patent No.: US 7,038,083 B2
(45) Date of Patent: May 2, 2006

(54) PROCESS FOR MAKING BISPHOSPHONIC ACIDS USING DILUENTS OTHER THAN HALOGENATED HYDROCARBONS

(75) Inventors: Rami Lidor-Hadas, Kfar Saba (IL); Zvi Harel, Kfar Saba (IL); Revital Lifshitz-Liron, Herzlia (IL); Eti Kovalevski, Netanya (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 10/442,001

(22) Filed: May 19, 2003

(65) Prior Publication Data

US 2004/0043967 A1    Mar. 4, 2004

Related U.S. Application Data

(60) Provisional application No. 60/450,193, filed on Feb. 25, 2003, provisional application No. 60/431,838, filed on Dec. 9, 2002, provisional application No. 60/423,337, filed on Nov. 1, 2002, provisional application No. 60/401,313, filed on Aug. 6, 2002, provisional application No. 60/381,284, filed on May 17, 2002.

(51) Int. Cl.
*C07F 9/02* (2006.01)
(52) U.S. Cl. .......................................... 564/15; 546/22
(58) Field of Classification Search .................. 564/15; 546/22
See application file for complete search history.

(56) References Cited

U.S. PATENT DOCUMENTS

| 4,407,761 A | 10/1983 | Blum et al. |
| 5,908,959 A | 6/1999 | Kubela et al. |

FOREIGN PATENT DOCUMENTS

| CA | 2018477 | 8/1995 |
| CA | 2044923 | 6/1996 |
| DE | 37 00 772 A1 | 7/1988 |
| EP | 0 402 152 | 12/1990 |
| GB | 2316945 | 3/1998 |
| WO | WO 98/34940 | 8/1998 |
| WO | WO 01/57052 | 8/2001 |
| WO | WO 02/090367 | 11/2002 |

OTHER PUBLICATIONS

Kieczykowski et al., "Preparation of (4-Amino-1-Hydroxybutylidene) bisphosphonic Acid Sodium Salt MD-217 (Alendronate Sodium). An Improved Procedure for the Preparation of 1-Hydroxy-1, 1-bisphosphonic Acids", *J. Org. Chem*, 60 (25)8310, 8311 (1995).

Robert Marcus, "Agents Affecting Calcification and Bone Turnover", in Goodman and Gilman's *The Pharmacological Basis of Therapeutics* 1519, 1537-1539 (Joel G. Hardman & Lee E. Limbird, eds. in chief, 9th ed., 1996).

*Primary Examiner*—Samuel Barts
(74) *Attorney, Agent, or Firm*—Kenyon & Kenyon LLP

(57) ABSTRACT

Provided is a novel method of making bisphosphonic acids, e.g. risedronic acid, including the step of combining a carboxylic acid, phosphorous acid, and a halophosphorous compound in the presence of a diluent that is an aromatic hydrocarbon or a silicone fluid. When the diluent is an aromatic hydrocarbon, a inert support or ortho-phosphoric acid codiluent is advantageously included.

16 Claims, No Drawings

PROCESS FOR MAKING BISPHOSPHONIC ACIDS USING DILUENTS OTHER THAN HALOGENATED HYDROCARBONS

CROSS-REFERENCE TO RELATED APPLICATION

This application claims the benefit of U.S. Provisional Applications Ser. No. 60/381,284, filed May 17, 2002; Ser. No. 60/401,313, filed Aug. 6, 2002; Ser. No. 60/423,337, filed Nov. 1, 2002, Ser. No. 60/431,838, filed Dec. 9, 2002 and Ser. No. 60/450,193, filed Feb. 25, 2003.

FIELD OF THE INVENTION

The present invention relates to a method of making bisphosphonic acids, salts of which are useful in the treatment of bone disorders.

BACKGROUND OF THE INVENTION

The bisphosponates, which are salts of bisphosphonic acids, are an important class of medicaments useful in the treatment of bone disorders such as Paget's disease and osteoporosis. See, e.g., Robert Marcus, *Agents Affecting Calcification and Bone Turnover*, in *Goodman and Gilman's The Pharmacological Basis of Therapeutics* 1519, 1537–39 (Joel G. Hardman & Lee E. Limbird, eds. in chief, $9^{th}$ ed., 1996). The sodium salt of risedronic acid (i.e. [1-hydroxy-2-(3-pyridinyl)ethylidene]bis[phosphonic acid] monosodium salt), marketed under the trade name Actonel® and the sodium salt of [4-amino-1-hydroxybutylidene]bis [phosphonic acid] are examples of pharmaceutically useful bisphosphonates.

The bisphosphonates are derived from the corresponding bisphosphonic acids. Several methods have been reported for preparing 1-hydroxy-1,1-bisphosphonic acids. The syntheses are based on reacting a carboxylic acid with a mixture of phosphorous acid and one of the following phosphorous halides: phosphorous trichloride ($PCl_3$), phosphorous oxychloride ($POCl_3$), phosphorous pentachloride ($PCl_5$), phosphorous tribromide ($PBr_3$), phosphorous oxybromide ($POBr_3$) or phosphorous pentabromide ($PBr_5$), then quenching the reaction mixture with water or a nonoxidizing aqueous acid, followed by heating to hydrolyze the phosphorous intermediates to the final product.

U.S. Pat. No. 4,407,761 describes a synthesis of 4-amino-1-hydroxybutylidene-1,1-bisphosphonic acid (alendronic acid) and other bisphosphonic acids. The reaction can be carried out in the presence of a diluent, especially chlorinated hydrocarbons, especially chlorobenzene, which does not solubilize the reaction components and serves only as a heat carrier. The reaction starts as a two-phase system, in which the melted phase gradually thickens into a non-stirrable mass. This semi-solid sticky mass finally turns into a hard, rigid material, coating the walls of the reaction vessel, fouling the reactor and preventing smooth heat transfer and complicating product work-up. This process might be suitable for laboratory preparation of gram quantities of the product however, for commercial production it is not acceptable. A solution to this caking and fouling problem is clearly required before the reaction can be economically practiced on a commercial scale.

The above-described flaws of the process of the '761 patent were acknowledged by Kieczykowski et al. See, e.g, Kieczykowski et al., *J. Org. Chem*, 60(25) 8310, 8311 (1995). In application for Canadian Patent 2,018,477 and 2,044,923, Kieczykowski et al. revealed a solution to the solidification and fouling problem. Methanesulfonic acid (MSA) was used to solubilize the reaction components and keep the reaction mixture fluid up to completion of the reaction. Although the problems with physical characteristics of the reaction appeared solved, a safety problem surfaced.

Methanesulfonic acid reacts with phosphorous trichloride and, under adiabatic conditions, the reaction becomes self-heating at 85° C. and an uncontrolled exotherm occurs at reaction temperatures >140° C. Kieczykowski et al. acknowledged this safety issue and raised it in Example 1 of both above-cited Canadian applications. The safety concern is mentioned by the authors in somewhat more detail in the above cited article in the Journal of Organic Chemistry.

U.S. Pat. No. 5,908,959 (corresponding to WO 98/34940), assigned to Apotex Inc., describes a process for preparing alendronic acid comprising reacting 4-aminobutyric acid (GABA) with phosphorous acid and phosphorous trichloride in the presence of a polyalkylene(glycol) or derivatives thereof. However, it was reported that large quantities of polyalkylene(glycol), as well as toluene, are required for the reaction, making it inefficient for use on a large scale.

There remains a need for a safe and efficient industrial process for preparing bisphosphonic acids, especially risedronic acid, alendronic acid, and zoledronic acid that is free of the solidification problem.

The present inventors have surprisingly found that yield is improved and fouling caused by solidification problems is reduced if, in the reaction between a carboxylic acid (e.g. 3-pyridyl acetic acid or its hydrochloride), $H_3PO_3$, and, for example, $POCl_3$, an aromatic hydrocarbon such as toluene, especially in the presence of ortho-phosphoric acid as codiluent, or a silicon oil such as polydimethylsiloxane, is used as a diluent instead of previously used halogenated hydrocarbons. The present inventors have also surprisingly found that the solidification and reactor fouling problem can be eliminated if the reaction between carboxylic acid, phosphorous acid, and, for example, $POCl_3$, is carried out in a diluent that is an aromatic hydrocarbon (e.g. toluene) in the presence of a heterogeneous solid support.

SUMMARY OF THE INVENTION

The present invention relates to a method of making a bisphosphonic acid and crystalline hydrates thereof including the step of combining a carboxylic acid with phosphorous acid and phosphorous oxychloride ($POCl_3$) in the presence of a diluent that is other than a halogenated hydrocarbon.

The diluents of the present invention include aromatic hydrocarbons such as toluene, xylene, and benzene, and inert silicone fluids such as polydimethylsiloxane ("PDMS") and polymethylphenylsiloxane ("PMPS"). The aromatic hydrocarbon diluents are not used with polyalkyene glycol codiluents.

In one aspect, the present invention relates to a method of making a bisphosphonic acid comprising the step of combining a carboxylic acid, phosphorous acid, and a halophosporous compound selected from $PCl_3$, $PCl_5$, $POCl_3$, $PBr_3$, $POBr_3$, and $PBr_5$, especially $POCl_3$, in the presence of a diluent that is an aromatic hydrocarbon, especially toluene, or a silicone fluid, especially a poly(dimethylsiloxane) with the proviso that, when the diluent is an aromatic hydrocarbon, a polyalkylene glycol is not present as a codiluent in the reaction mixture.

In another aspect, the present invention relates to a method of making a bisphosphonic acid comprising the step of combining a carboxylic acid, phosphorous acid, and a halophosporous compound selected from $PCl_3$, $PCl_5$, $POCl_3$, $PBr_3$, $POBr_3$, and $PBr_5$ in the presence of a diluent that is an aromatic hydrocarbon or a silicone fluid, and a codiluent that is ortho-phosphoric acid, with the proviso that, when the diluent is an aromatic hydrocarbon, a polyalkylene glycol is not present as a codiluent in the reaction mixture.

In another aspect, the present invention relates to a method of making a bisphosphonic acid comprising the step of combining a carboxylic acid, phosphorous acid, and a halophosporous compound selected from $PCl_3$, $PCl_5$, $POCl_3$, $PBr_3$, $POBr_3$, and $PBr_5$ in the presence of a diluent that is an aromatic hydrocarbon or a silicone fluid, with the proviso that, when the diluent is an aromatic hydrocarbon, a polyalkylene glycol is not present as a codiluent in the reaction mixture, and in the presence of a heterogeneous solid support.

In yet another aspect, the present invention relates to method of making a bisphosphonic acid comprising the step of combining a carboxylic acid, phosphorous acid, and a halophosporous compound selected from $PCl_3$, $PCl_5$, $POCl_3$, $PBr_3$, $POBr_3$, and $PBr_5$ in the presence of a diluent that is an aromatic hydrocarbon or a silicone fluid, with the proviso that, when the diluent is an aromatic hydrocarbon, a polyalkylene glycol is not present as a codiluent in the reaction mixture, wherein the phosphorous acid and the second phosphorous compound that is a halophosphorous compound are added in at least first and second portions.

In another aspect, the present invention relates to a method of making a bisphosphonic acid comprising the step of combining a carboxylic acid selected from 4-aminobutanoic acid, (3-pyridyl)ethanoic acid, (1-imidazoyl)ethanoic acid, N-(n-pentyl)-N-methyl-3-aminopropanoic acid, 2(imidazo[1,2-a]pyridin-3-yl)ethanoic acid, and 6-aminohexanoic acid, and the hydrochlorides thereof, phosphorous acid, and a halophosporous compound selected from $PCl_3$, $PCl_5$, $POCl_3$, $PBr_3$, $POBr_3$, and $PBr_5$, especially $POCl_3$, in the presence of a diluent that is an aromatic hydrocarbon, especially toluene, or a silicone fluid, especially poly(dimethylsiloxane) with the proviso that, when the diluent is an aromatic hydrocarbon, a polyalkylene glycol is not present as a codiluent in the reaction mixture. When the diluent is an aromatic hydrocarbon, a heterogeneous solid support and/or ortho-phosphoric acid can also be advantageously included in the combination.

In still a further aspect, the present invention relates to a method of making alendronic acid monohydrate comprising the steps of:
a) combining 4-aminobutanoic acid, phosphorous acid, and a halophosporous compound selected from $PCl_3$, $PCl_5$, $POCl_3$, $PBr_3$, $POBr_3$, and $PBr_5$ at a temperature of about 80° C. to about 100° C. in the presence of a diluent that is an aromatic hydrocarbon or a silicone fluid to form a reaction mixture, with the proviso that, when the diluent is an aromatic hydrocarbon, a polyalkylene glycol is not present as a codiluent in the reaction mixture, optionally including ortho-phosphoric acid codiluent, or, when the diluent is an aromatic hydrocarbon, a heterogeneous solid support
b) combining the reaction mixture with water, whereby an aqueous and a non-aqueous phase are formed,
c) separating the aqueous phase,
d) combining the aqueous phase with ethanol whereby a suspension comprising alendronic acid is formed, and
e) isolating alendronic acid monohydrate from the suspension.

In another aspect, the present invention relates to a method of making risedronic acid monohydrate comprising the steps of:
a) combining (3-pyridyl)ethanoic acid or its hydrochloride salt, phosphorous acid, and a halophosporous compound selected from $PCl_3$, $PCl_5$, $POCl_3$, $PBr_3$, $POBr_3$, and $PBr_5$ at a temperature of about 80° C. to about 100° C. in the presence of a diluent that is an aromatic hydrocarbon or a silicone fluid to form a reaction mixture, with the proviso that, when the diluent is an aromatic hydrocarbon, a polyalkylene glycol is not present as a codiluent in the reaction mixture, optionally including ortho-phosphoric acid codiluent or, when the diluent is an aromatic hydrocarbon, a heterogeneous solid support,
b) combining the reaction mixture with water, whereby an aqueous and a non-aqueous phase are formed,
c) separating the aqueous phase,
d) combining the aqueous phase with ethanol whereby a suspension comprising risedronic acid is formed, and
e) isolating risedronic acid monohydrate from the suspension.

In a further aspect, the present invention relates to A method of making zoledronic acid monohydrate comprising the steps of:
a) combining (1-imidazoyl)ethanoic acid or its hydrochloride, phosphorous acid, and a halophosporous compound selected from $PCl_3$, $PCl_5$, $POCl_3$, $PBr_3$, $POBr_3$, and $PBr_5$ at a temperature of about 80° C. to about 100° C. in the presence of a diluent that is an aromatic hydrocarbon or a silicone fluid to form a reaction mixture, with the proviso that, when the diluent is an aromatic hydrocarbon, a polyalkylene glycol is not present as a codiluent in the reaction mixture, optionally including ortho-phosphoric acid codiluent or, when the diluent is an aromatic hydrocarbon, a heterogeneous solid support,
b) combining the reaction mixture with water, whereby an aqueous and a non-aqueous phase are formed,
c) separating the aqueous phase,
d) combining the aqueous phase with ethanol whereby a suspension comprising zoledronic acid is formed, and
e) isolating zoledronic acid monohydrate from the suspension.

In another aspect, the present invention relates to A method of making ibandronic acid comprising the steps of:
a) combining N-methyl-N-(n-pentyl)-3-aminopropanoic acid, phosphorous acid, and a halophosporous compound selected from $PCl_3$, $PCl_5$, $POCl_3$, $PBr_3$, $POBr_3$, and $PBr_5$ at a temperature of about 80° C. to about 100° C. in the presence of a diluent that is an aromatic hydrocarbon or a silicone fluid to form a reaction mixture, with the proviso that, when the diluent is an aromatic hydrocarbon, a polyalkylene glycol is not present as a codiluent in the reaction mixture, optionally including ortho-phosphoric acid codiluent or, when the diluent is an aromatic hydrocarbon, a heterogeneous solid support,
b) combining the reaction mixture with water, whereby an aqueous and a non-aqueous phase are formed,
c) separating the aqueous phase,
d) combining the aqueous phase with ethanol whereby a suspension comprising ibandronic acid is formed, and
e) isolating ibandronic acid from the suspension.

In still a further aspect, the present invention relates to A method of making minodronic acid hemihydrate comprising the steps of:
a) combining 2-(imidazo[1,2-a]pyridin-3-yl)ethanoic acid, phosphorous acid, and a halophosporous compound selected from $PCl_3$, $PCl_5$, $POCl_3$, $PBr_3$, $POBr_3$, and $PBr_5$ at a temperature of about 80° C. to about 100° C. in the presence of a <<diluent>> that is an aromatic hydrocarbon or a silicone fluid to form a reaction mixture, with the proviso that, when the diluent is an aromatic hydrocarbon, a polyalkylene glycol is not present as a codiluent in the reaction mixture, optionally including ortho-phosphoric acid codiluent or, when the diluent is an aromatic hydrocarbon, a heterogeneous solid support,
b) combining the reaction mixture with water, whereby an aqueous and a non-aqueous phase are formed,
c) separating the aqueous phase,
d) combining the aqueous phase with ethanol whereby a suspension comprising minodronic acid is formed, and
e) isolating minodronic acid from the suspension.

In yet a further aspect, the present invention relates to method of making neridronic acid comprising the steps of:
a) combining 6-aminohexanoic acid, phosphorous acid, and a halophosporous compound selected from $PCl_3$, $PCl_5$, $POCl_3$, $PBr_3$, $POBr_3$, and $PBr_5$ at a temperature of about 80° C. to about 100° C. in the presence of a <<diluent>> that is an aromatic hydrocarbon or a silicone fluid to form a reaction mixture, with the proviso that, when the diluent is an aromatic hydrocarbon, a polyalkylene glycol is not present as a codiluent in the reaction mixture, optionally including ortho-phosphoric acid codiluent or a heterogeneous solid support,
b) combining the reaction mixture with water, whereby an aqueous and a non-aqueous phase are formed,
c) separating the aqueous phase,
d) combining the aqueous phase with ethanol whereby a suspension comprising neridronic acid is formed, and
e) isolating minodronic acid from the suspension.

DETAILED DESCRIPTION OF THE INVENTION

As used herein in connection with a measured quantity, the term about refers to that variation in the measured quantity as would be expected by the skilled artisan making the measurement and exercising a level of care commensurate with the objective of the measurement and the precision of the measuring equipment used.

As used herein, the abbreviation TGA refers to the well-known technique of thermogravimetric analysis. The results of TGA analysis disclosed herein were obtained using a Metler—Toledo Star$^e$ system at a heating rate of 10° per minute with 40 mL/min nitrogen purge gas. Sample weights were approximately 10 mg.

The present invention provides a method for making bisphosphonic acids of general formula:

$(HO)_2P(O)-C(OH)R_1-P(O)(OH)_2$  I

In preferred embodiments, $R_1$ is $R_2CH_2$— and $R_2$ can be C1 to C8 linear or branched alkyl, optionally bearing one or more substituents selected from amino, hydroxy, halo, aryl, heteroaryl, haloaryl, haloheteroaryl; or $R_2$ can be aryl or heteroaryl, optionally substituted with one or more substituents selected from amino, hydroxy, halo, aryl, heteroaryl, haloaryl, and haloheteroaryl. In particularly preferred embodiments, $R_2$ is either 2-aminoethyl (i.e. I is alendronic acid), 3-pyridyl (i.e. I is risedronic acid), imidazol-1-yl (i.e. I is zoledronic acid), n-$C_5H_{11}$—N($CH_3$)$CH_2$— (i.e. I is ibandronic acid), imidazo[1,2-a]pyridine-3-yl (i.e. I is minodronic acid), or 4-aminobutyl (i.e. I is neridronic acid).

When $R_2$ is either 2-aminoethyl, 3-pyridyl, or 1H-imidazol-1-yl, the product obtained from the practice of the method of the present invention is a crystalline monohydrate of the bisphosphonic acid. The crystalline monohydrates of risedronic acid, alendronic acid, and zoledronic acid are particular embodiments of the present invention.

In the method of the present invention, I are made by reacting a carboxylic acid (or, in the case of an amino acid or other acid having a quaternarizable nitrogen atom, optionally the hydrochloride) with phosphorous acid ($H_3PO_3$) and a second phosphorous compound that is preferably a halophosohorous compound (phosphorous halide) selected from $PCl_3$, $PCl_5$, $POCl_3$, $PBr_3$, $POBr_3$, and $PBr_5$, in the presence of a diluent that is other than a halogenated hydrocarbon. Phosphorous oxychloride, $POCl_3$, is the preferred halophosphorous compound. Any carboxylic acid can be used in the practice of the present invention. 4-Aminobutanoic acid (γ-aminobutyric acid), 2-(pyridin-3-yl)ethanoic acid (3-pyridine acetic acid), 1-carboxymethylimidazole (1H-imidazol-1-yl acetic acid), N-pentyl-N-methyl-3-aminopropanoic acid, 2(imidazo[1,2-a]pyridin-3-yl)ethanoic acid, and 6-aminohexanoic acid, or hydrochlorides thereof, are preferred carboxylic acids in the practice of the present invention.

Preferably, 1.25 to 4 equivalents of $H_3PO_3$ and about 2 to about 4 equivalents of second phosphorous compound are used per equivalent of carboxylic acid. The diluent, which can also be referred to as a slurrying agent, can be used in an amount between about 5 and about 8 volumes per weight [volumes per weight is milliliters per gram or liters per kilogram] of carboxylic acid, preferably about 5.5 volumes per weight [i.e. mL per g] of carboxylic acid. The skilled artisan will know to adjust the amount of diluent according to, among other things, the particular reactor being used and the viscosity of the reaction mixture.

The diluents of the present invention are selected from the group consisting of the aromatic hydrocarbons or from the group consisting of inert silicon oils, also called silicone fluids. Aromatic hydrocarbons are normally liquid at about 25° C. Toluene is a preferred aromatic hydrocarbon diluent of the present invention. Other aromatic hydrocarbons useful in the practice of the present invention include benzene and the xylenes. Toluene is the preferred aromatic hydrocarbon for use in the present invention.

When the diluent is an aromatic hydrocarbon, a polyalkylene glycol is not used as a codiluent (combined with the aromatic hydrocarbon). Polyalkylene glycols have the general structure $R_1$—(Q—$CH_2$—O—)$_n$—$R_2$, where $R_1$ and $R_2$ are the same or different and equal to hydrogen, lower alkyl, and lower acyl; Q is CH($CH_3$) or —$CH_2$; and n is about 4 to about 250.

The silicon oils of the present invention include poly(dimethylsiloxane), "PDMS", a polymeric compound composed of repeating dimethylsiloxane units: —[Si($CH_3$)$_2$—O—]$_n$. PDMS is the preferred silicon oil of the present invention. Another type of silicon oil included in the present invention is poly(methylphenylsiloxane), "PMPS", a compound composed of repeating methylphenylsiloxane units: —[($CH_3$)($C_6H_5$)Si—O—]$_n$.

Silicon oils, also known as silicone fluids, are particularly suited as diluents or slurrying agents in the present invention because they are stable over a wide temperature range and are also non-toxic and therefore useful in the pharmaceutical industry. Silicon oil effectively dissolves the phosphorus acid and halophosphorous compound, however it does not dissolve the carboxylic acid in the reaction. The carboxylic acid remains suspended in the silicon oil; thus at least one reactant is in suspension.

The silicon oils useful in the practice of the present invention are miscible with benzene, toluene, carbon tetrachloride and other organic solvents, but are insoluble in water and are therefore easily removed before hydrolysis in the present invention. Separation of silicon oil is also facilitated by adding toluene at the end of the reaction. Examples of silicone fluids useful in the practice of this invention include, but are not limited to, polydimethylsiloxane ("PDMS"), poly[oxy(dimethylsilene)], dimethicone, methylsilicone oil, Dow Corning® 200 fluid (a poly(dimethylsiloxane)); Wacker SWS101 fluid (a poly(dimethylsiloxane)); Baysilone® MPH 350 fluid; poly[oxy(methylphenylsilylene)]; methylphenyl silicone oil; and Dow Corning® 710 fluid (phenyl methylsiloxane)

A heterogeneous solid support is a particulate solid, essentially insoluble in aliphatic or aromatic hydrocarbons, chlorinated aliphatic or aromatic hydrocarbons, or polar aprotic solvents, having sufficient adsorptive capacity so that when used in a deposition inhibiting effective amount in combination with a diluent that is an aromatic hydrocarbon, fouling of the reactor and agitator with solid of intermediate products in the heterogeneous synthesis of bisphosphonic acids according to the present invention from a carboxylic acid, $H_3PO_3$, and a second phosphorous compound in the presence of a diluent that is an aromatic hydrocarbon, e.g. toluene, chlorobenzene and the like as described below, does not occur.

Preferred heterogeneous solid supports have a porous structure and include fumed silica, silica xerogels, and diatomaceous silica. Diatomaceous silica having a median pore size between about 5μ and about 9μ, preferably about 7μ, is a particularly preferred heterogeneous solid support. Hyfllo Super-Cel, available from World Minerals, Santa Barbara, Calif., USA, is an example of a preferred heterogeneous solid support.

The skilled artisan will know to adjust the amount of heterogeneous solid support used according to, among other things, the porosity and effective surface area of the heterogeneous solid support. When the heterogeneous solid support has a nominal pore size of about 7μ, the support will be used in a amount between about 30 wt-% and about 50 wt-% of the combined weight of all reactants.

In one embodiment, the present invention provides a method of making a bisphosphonic acid that includes the step of combining—in a two-phase system—a carboxylic acid, phosphorous acid ($H_3PO_3$), and a second phosphorous compound that is a halophosphorous compound in the presence of a diluent that is an aromatic hydrocarbon, preferably toluene, in the substantial absence of a polyalkylene glycol. It is preferred to slowly add the second phosphorous compound (e.g. $POCl_3$) in small aliquots (or dropwise) to a mixture of carboxylic acid, $H_3PO_3$, and diluent.

The combining is carried out in a suitable reactor with good agitation at a temperature between about 65° C. and about 100° C., preferably at about 100° C., for a time between about 1 and about 4 hours. A time of about 2.5 hours is usually sufficient and is preferred. During the reaction, a solid forms and the reaction mixture can be multi-phased.

Following the reaction, water is combined with the reaction mixture, whereby aqueous and nonaqueous phases are formed, and the resulting combination is heated to a temperature between about 60° C. and about 80C to dissolve the solid. The amount of water can be from about one to about three times the volume, preferably one, of diluent used. The aqueous phase is then separated and heated to a temperature between about 90° C. and about 100° C. for about 8 to about 24 hours, preferably 16 hours, whereafter the product bisphosphonic acid can be isolated from the aqueous phase by any means known in the art.

The product bisphosphonic acid can be isolated, for example, by combining the aqueous phase with ethanol to precipitate the product and, optionally cooling the resulting suspension to about 5° C. The product bisphosphonic acid can then be separated from the suspension by any means known in the art, for example by filtration (gravity or suction) or centrifugation/decanting, to mention just two. The yield of dried product in this embodiment can be 70% to 80% or more, an improvement relative to known methods.

In another embodiment, the present invention provides a method of making a bisphosphonic acid that includes the step of combining—in a two-phase system—a carboxylic acid, phosphorous acid, and a second phosphorous compound in the presence of a diluent that is an inert silicon oil, preferably polydimethylsiloxane (PDMS). It is preferred to slowly add the second phosphorous compound (e.g. $POCl_3$) in small aliquots (or dropwise) to a mixture of carboxylic acid, $H_3PO_3$, and diluent.

The combining is carried out in a suitable reactor with good agitation at a temperature between about 65° C. and about 100° C., preferably at about 80° C., for a total time between about 15 and about 30 hours. A time greater than 20 hours is preferred and about 25 hours is particularly preferred.

Following the reaction, water and, optionally, toluene are combined with the reaction mixture, whereby aqueous and nonaqueous phases are formed, and the resulting combination is heated to a temperature between about 70° C. and about 80° C. to dissolve the solid. The amount of water and, when used, toluene are not critical and can be from about one to about three, preferably one, times the volume of diluent used. The mixture is then stirred vigorously for about 10 to 40 minutes. The aqueous phase is then separated from the toluene phase (containing the silicon oil) and heated to a temperature between about 90° C. and about 100° C. for about 4 to about 20 hours, preferably 16 hours, whereafter the product bisphosphonic acid can be isolated from the aqueous phase by any means known in the art.

The product bisphosphonic acid can be isolated, for example, by adding ethanol to the aqueous phase to precipitate the product and, optionally and preferably, cooling the resulting suspension to about 5° C. The product bisphosphonic acid can then be separated from the suspension by any means known in the art, for example by filtration (gravity or suction) or centrifugation/decanting, to mention just two. The yield of dried product in this embodiment can be 60% to 80% or more, an improvement relative to known methods.

In another embodiment, the present invention provides a method of making a bisphosphonic acid including the step of combining a carboxylic acid, $H_3PO_3$, and a second phosphorous compound that is a halophosphorous compound in the presence of a diluent that is an aromatic hydrocarbon, essentially free of polyalkylene glycol, and ortho-phosphoric acid ($H_3PO_4$) codilvent, whereby the reaction mixture remains stirrable and the reactor remains substantially free of fouling deposits during the reaction. It is preferred to add the second phosphorous compound (e.g. $POCl_3$) in small aliquots (or dropwise) to a mixture of carboxylic acid, $H_3PO_3$, $H_3PO_4$, and diluent.

The diluent can be used in an amount between about 5 and about 8 volumes per weight of carboxylic acid, preferably about 7.2 volumes per weight of carboxylic acid. The skilled artisan will know to adjust the amount of diluent according to, among other things, the particular reactor being used.

The ortho-phosphoric acid is used in amount equal to between about 3 and about 6, preferably 5, equivalents, based on the amount of carboxylic acid used.

The combining is carried out in a suitable reactor with good agitation at a temperature between about 65° C. and about 100° C., preferably 100° C., for a time of about 2 hours or more, preferably 16 to 20 hours.

Following the reaction, water is combined with the fluid reaction mixture at a temperature between about 60° C. and about 90° C., whereby aqueous and nonaqueous phases are formed, and the combined reaction mixture and water are stirred until no solid is visible in the combination. The amount of water can be from about one to about three, preferably one, times the volume of diluent used. The aqueous phase is separated and stirred for a time at a temperature between about 90° C. and about 100° C., preferably 95° C. The time is not critical as long as it is sufficient to allow formation of the desired product. A time of 5 to 20 hours is typically sufficient.

The desired bisphosphonic acid product can be isolated from the aqueous phase by any means known in the art. For example, the bisphosphonic acid can be isolated by adding ethanol to the aqueous phase and, optionally, cooling the suspension so obtained to a temperature of about 5° C. The bisphosphonic acid can be separated from the suspension by any means known to the skilled artisan, for example filtration (gravity or suction), or centrifugation/decanting, to mention just two. In this embodiment, the yield can be 68% or more.

In yet another and preferred embodiment, the present invention provides a method of making a bisphosphonic acid including the step of combining a carboxylic acid, $H_3PO_3$, and a second phosphorous compound that is a halophosphorous compound (preferably $POCl_3$), in the presence of a diluent that is an aromatic hydrocarbon, and a heterogeneous solid support, preferably diatomaceous silica.

The diluent, preferably toluene, can be used in an amount between about 5 and about 8 volumes per weight of carboxylic acid, preferably about 7.2 volumes per weight of carboxylic acid. The skilled artisan will know to adjust the amount of diluent according to the particular reactor being used. The heterogeneous solid support can be used in an amount equal to between 30 and about 50 percent of the total weight of carboxylic acid, $H_3PO_3$, and second phosphorous compound.

The combining is carried out in a suitable reactor having good agitation at a temperature between about 65° C. and about 100° C., preferably 100° C., for a time of about 4 to about 8 hours. It is convenient to add the second phosphorous compound in small portions or dropwise to a suspension of heterogeneous solid support in diluent and the remaining reactants. The reactor remains essentially free of fouling deposits.

Following the reaction, water is combined with the suspension, whereby aqueous and nonaqueous phases form and the combination of water and suspension is held at about 65° C. for a time sufficient to bring the product into aqueous solution, typically 20 minutes to one hour. The liquid phases (aqueous and nonaqueous) are separated from the heterogeneous solid support. The aqueous phase is separated. If desired, the heterogeneous solid support can be washed with additional aliquots of hot water and the washings combined with the separated aqueous phase. The aqueous phase (and washings if any) is heated at 90° C. to 95° C. and stirred at this temperature for 5 to 20 hours.

The product bisphosphonic acid can be isolated from the aqueous phase by any means known in the art. For example, ethanol (1 to 2 times the volume of the aqueous phase) can be added to cooled (25° C.) aqueous phase and, optionally and preferably, the resulting suspension is cooled to about 5° C. The bisphosphonic acid can be separated from the suspension by any means known in the art, for example filtration (gravity or suction) or centrifugation/decanting, to mention just two. The yield of dried product in this embodiment can be 56% or more.

In still another and preferred embodiment, the present invention provides a method of making a bisphosphonic acid that includes the step of combining a carboxylic acid, first and second portions of phosphorous acid ($H_3PO_3$) and first and second portions of a second phosphorous compound that is a halophosphorous compound (preferably $POCl_3$) in the presence of a diluent that is an aromatic hydrocarbon, preferably toluene. This embodiment includes the additional step of adding a second portion (amount) of phosphorous acid ($H_3PO_3$) and a second portion (amount) of second phosphorous compound that is a halophosphorous compound in a stepwise or incremental manner. A stepwise or incremental manner means that a part of the second portion of $H_3PO_3$ and second portion of second phosphorous compound or both is added, then the resultant reaction mixture is heated (between 65° C. and 100° C.), for a time increment of between 1 and 4 hours. The cycle is repeated until the desired total second amount of $H_3PO_3$ and second phosphorous compound has been added.

It is preferred to add the second phosphorous compound (e.g. $POCl_3$) in small aliquots (or dropwise) initially to a mixture of carboxylic acid, $H_3PO_3$, and diluent, to form the initial reaction mixture. It is also preferred to add to the initial reaction mixture a second amount of both $H_3PO_3$ and the second phosphorous compound in a stepwise or incremental manner, and to add them in two or more increments.

The combining is carried out in a suitable reactor with good agitation and at a temperature between about 65° C. and 100° C., preferably at about 100° C. The initial reaction mixture, formed by the dropwise addition of the second phosphorous compound to a mixture of carbolyic acid, $H_3PO_3$, and diluent, is then heated for an initial time increment between about 1 and about 3 hours, preferably about 2 hours.

In preferred embodiments, the $H_3PO_3$ and the second phosphorous compound are added in at least first and second portions. After addition of a first portion, a second portion of $H_3PO_3$ and a second portion of second phosphorous compound that is a halophosphorous compound are then added in aliquots (dropwise) in an incremental manner, with time increments of between 1 and about 4 hours between slow addition of first and second portions. The total reaction time, obtained from adding each incremental time to the initial time increment, is preferably between about 3 and 6 hours. It is preferred to add a second portion of both $H_3PO_3$ and second phosphorous compound in two distinct steps. The preferred amount of a second amount of $H_3PO_3$ added in each increment is equal to about one-third of the volume of $H_3PO_3$ present in the initial reaction mixture. The preferred amount of a second portion of second phosphorous compound is equal to about one-third of the volume of second phosphorous compound added to the initial reaction mixture.

Following the reaction, water is combined with the reaction mixture, whereby aqueous and nonaqueous phases form, and the resulting combination is heated to a temperature between about 60° C. and about 70° C. to dissolve the solid. The amount of water can be from about one to about three, preferably one, times the volume of diluent used. The aqueous phase is then separated and heated to a temperature between about 90° C. and about 100° C. for about 8 to about 24 hours, preferably 16 hours, whereafter the product bisphosphonic acid can be isolated from the aqueous phase by any means known in the art.

For example, the product bisphosphonic acid can be isolated by combining the aqueous phase with ethanol to precipitate the product and, optionally, cooling the resulting suspension to about 5° C. The product bisphosphonic acid can then be separated from the suspension by any means known in the art, for example by filtration (gravity or suction) or centrifugation/decanting, to mention just two. The yield of dried product in this embodiment can be 70% to 80% or more, an improvement relative to known methods.

In another preferred embodiment, the present invention provides a method of making a bisphosphonic acid that includes the step of combining a carboxylic acid, a phosphorous acid ($H_3PO_3$) and a second phosphorous compound that is a halophosphorous compound (preferably $POCl_3$) in the presence of a diluent selected from inert silicon oils, preferably PDMS, and the additional step of adding a second portion of phosphorous acid ($H_3PO_3$) and a second portion of second phosphorous compound. The temperature of the reaction mixture can be cycled between additions.

It is preferred to add the second phosphorous compound (e.g. $POCl_3$) in small aliquots (or dropwise) initially to a mixture of carboxylic acid, $H_3PO_3$, and diluent, to form the initial reaction mixture. It is also preferred to add to the initial reaction mixture a second amount of both $H_3PO_3$ and the second phosphorous compound in a stepwise or incremental manner, and to add them in two or more increments.

The combining is carried out in a suitable reactor with good agitation and at a temperature between about 65° C. and 100° C., preferably at about 70° C. The initial reaction mixture, formed by the dropwise addition of the second phosphorous compound to a mixture of carboxylic acid, $H_3PO_3$, and diluent, is then heated for an initial time increment between about 2 and about 20 hours, preferably about 4 hours.

A second portion (amount) of $H_3PO_3$ and a second portion (amount) of second phosphorous compound or both are then slowly added in small aliquots in an incremental manner with time increments of between 2 and about 20 hours between the additions of the second portion of $H_3PO_3$ and the second portion of halophosphorous. The total reaction time, obtained from adding each incremental time to the initial time increment, is preferably between about 20 and 30 hours. It is preferred to add a second portion of both $H_3PO_3$ and second phosphorous compound in two steps. The preferred second portion of $H_3PO_3$ added in each increment is equal to about one-third of the volume of $H_3PO_3$ present in the initial reaction mixture. The preferred second amount of second phosphorous compound is equal to about one-third of the volume of second phosphorous compound added dropwise to form the initial reaction mixture.

Following the reaction, water and, if desired, toluene are combined with the reaction mixture, whereby aqueous and nonaqueous phases form, and the resulting combination is heated to a temperature between about 60° C. and about 80° C. to dissolve the solid. Addition of toluene is advantageous if the viscosity of the reaction mixture is too high. When used, the amount of toluene is adjusted according to the viscosity of the reaction mixture. The amount of water can be from about one to about three, preferably one, times the volume of diluent used. The mixture is then stirred vigorously for about 10 to 40 minutes. The aqueous phase is then separated and heated to a temperature between about 90° C. and about 100° C. for about 8 to about 24 hours, preferably 16 hours, whereafter the product bisphosphonic acid can be isolated from the aqueous phase by any means known in the art.

For example, the product bisphosphonic acid can be isolated by combining the aqueous phase with ethanol to precipitate the product and, optionally, cooling the resulting suspension to about 5° C. The product bisphosphonic acid can then be separated from the suspension by any means known in the art, for example by filtration (gravity or suction) or centrifugation/decanting, to mention just two. The yield of dried product in this embodiment can be 70% to 80% or more, an improvement relative to known methods.

When 4-aminobutanoic acid is used in the method of the present invention, in any of its embodiments discussed above, the product is a crystalline monohydrate of alendronic acid. When 2-(3-pyridin-3-yl)ethanoic acid is used in the method of the present invention, in any of its embodiments discussed above, the product is a crystalline monohydrate of risedronic acid. When 1H-imidazole-1-yl acetic acid is used in the method of the present invention, in any of its embodiments, the product is a crystalline monohydrate of zoledronic acid. When the carboxylic acid is N-(n-pentyl)-N-methyl-3-aminopropanoic acid is used, the isolated bisphosphonic acid is ibandronic acid. When 2-(imidazo[1,2-a]pyridin-2-yl)ethanoic acid is used in the method of the present invention, in any of its embodiments, minodronic hemihydrate acid is obtained. When 6-aminohexanoic acid is used in the practice of the present invention, in any of its embodiments, neridronic acid is obtained.

The present invention can be illustrated with the follow non-limiting examples.

EXAMPLE 1

A 250 ml cylindrical reactor equipped with a mechanical stirrer, a thermometer, a reflux condenser and a dropping funnel, was charged with 3-pyridine acetic acid hydrochloride (6.94 g, 0.04 mole), phosphorous acid (9.84 g, 0.12 mole) and toluene (50 ml). The suspension was heated to 85° C. and phosphorous oxychloride (11.2 ml, 0.12 mole) was added dropwise during 20 minutes. The reaction mixture was then heated to 95° C. for 2.5 hours. Water (50 ml) was added after cooling the reaction mixture to 65° C. The mixture was stirred vigorously until the solidified product dissolved completely. The toluene and the aqueous phases were separated and the aqueous phase was heated at 95° C. for 16 hours. Then aqueous phase it was cooled to 25° C. and absolute ethanol (100 ml) was added to precipitate the final product. The suspension was cooled to 5° C. and held at that temperature for 1 hour. The white product was filtered, washed with absolute ethanol (2×50 ml) and dried in a vacuum oven at 50° C. for 20 hours to obtain 9.34 g (82%) of risedronic acid monohydrate.

EXAMPLE 2

A 250 ml cylindrical reactor equipped with a mechanical stirrer, a thermometer, a reflux condenser and a dropping funnel, was charged with 3-pyridine acetic acid hydrochloride (6.94 g, 0.04 mole), phosphorous acid (9.84 g, 0.12 mole) and silicon oil (Aldrich) (50 ml). The suspension was heated to 85° C. and phosphorous oxychloride (11.2 ml, 0.12 mole) was added dropwise during 45 minutes. The reaction mixture was then heated to 95° C. for 25 hours. Then another amount of phosphorous oxychloride (3.73 ml, 0.04 mole) was added dropwise and the reaction mixture was heated for an additional 5 hours at 95° C. Water (50 ml) and toluene (50 ml) were added after cooling the reaction mixture to 65° C. The mixture was stirred vigorously for 30 minutes. Then the toluene phase (containing the silicon oil) and the aqueous phases were separated and the aqueous phase was heated at 95° C. for 16 hours. Then the aqueous phase was cooled to 5° C. and was stirred at this temperature for 5.5 hours. The white product was filtered, washed with water (2×50 ml) and dried in a vacuum oven at 50° C. for 11 hours to obtain 7.19 g (59%) of risedronic acid monohydrate.

[Remark: The yield of the above process is calculated on dry base].

EXAMPLE 3

A 250 ml cylindrical reactor equipped with a mechanical stirrer, a thermometer, a reflux condenser and a dropping funnel, was loaded with 3-Pyridine acetic acid hydrochloride (6.94 g, 0.04 mole), phosphorous acid (9.84 g, 0.12 mole) and silicon oil (silicon fluid M-350) (50 ml). The suspension was heated to 85° C. and phosphorous oxychloride (11.2 ml, 0.12 mole) was added dropwise during 30 minutes. The reaction mixture was then heated to 95° C.–100° C. After 4 hours at 95° C.–100° C., another amount of phosphorous oxychloride (3.73 ml, 0.04 mole) and phosphorous acid (3.28 g, 0.04 mole) was added and the reaction mixture was heated at 95° C.–100° C. for additional 17 hours. Water (50 ml) and toluene (50 ml) were added after cooling the reaction mixture to 65° C. The mixture was stirred vigorously for 10 minutes. Then the toluene phase (containing the silicon oil) and the aqueous phase were separated and the aqueous phase was heated at 95° C. for 18 hours. Then it was cooled to 5° C. and absolute ethanol (50 ml) was added. The mixture was stirred at this temperature for 4 hours. The white product was then filtered, washed with absolute ethanol (2×50 ml) and dried in a vacuum oven at 50° C. for 22 hours to give 6.18 g (51%) of risedronic acid monohydrate.

[Remark: The yield of the above process is calculated on dry base].

EXAMPLE 4

A 250 ml cylindrical reactor equipped with a mechanical stirrer, a thermometer, a reflux condenser and a dropping funnel, was loaded with 3-pyridine acetic acid hydrochloride (6.94 g, 0.04 mole), phosphorous acid (9.84 g, 0.12 mole) and silicon oil (Merck) (50 ml). The suspension was heated to 84° C. and phosphorous oxychloride (11.2 ml, 0.12 mole) was added dropwise during 30 minutes. After 4 hours at 84° C., another amount of phosphorous oxychloride (3.73 ml, 0.04 mole) and phosphorous acid (3.28 g, 0.04 mole) was added and the reaction mixture was heated at 84° C. for additional 20 hours. Water (50 ml) and toluene (50 ml) were added after cooling the reaction mixture to 65° C. The mixture was stirred vigorously for 20 minutes. Then the toluene phase (containing the silicon oil) and the aqueous phase were separated and the aqueous phase was heated at 95° C. for 16 hours. Then it was cooled to 5° C. and absolute ethanol (50 ml) was added. The mixture was stirred at this temperature for 4 hours. The white product was then filtered, washed with absolute ethanol (2×75 ml) and dried in a vacuum oven at 50° C. for 26 hours to give 9.30 g (76%) of risedronic acid monohydrate.

[Remark: The yield of the above process is calculated on dry base].

EXAMPLE 5

A 250 ml cylindrical reactor equipped with a mechanical stirrer, a thermometer, a reflux condenser and a dropping funnel, was loaded with 3-Pyridine acetic acid hydrochloride (6.94 g, 0.04 mole), ohosphorous acid (9.84 g, 0.12 mole) and silicon oil (Merck) (50 ml). The suspension was heated to 70° C. and phosphorous oxychloride (11.2 ml, 0.12 mole) was added dropwise during 20 minutes. After 4 hours at 70° C., another amount of phosphorous oxychloride (3.73 ml, 0.04 mole) and phosphorous acid (3.28 g, 0.04 mole) was added and the reaction mixture was heated at 70° C. for additional 2 hours. Then another amount of phosphorous oxychloride (3.73 ml, 0.04 mole) and phosphorous acid (3.28 g, 0.04 mole) was added and the reaction mixture was heated at 70° C. for additional 16 hours. Water (50 ml) and toluene (50 ml) were added after cooling the reaction mixture to 65° C. The mixture was stirred vigorously for 10 minutes. Then the toluene phase (containing the silicon oil) and the aqueous phase were separated and the aqueous phase was heated at 95° C. for 16 hours. Then it was cooled to 25° C. and absolute ethanol (50 ml) was added. The mixture was cooled to 5° C. and was stirred at this temperature for 3 hours. The white product was then filtered, washed with absolute ethanol (2×45 ml) and dried in a vacuum oven at 50° C. for 24 hours to give 9.41 g (77%) of risedronic acid monohydrate.

[Remark: The yield of the above process is calculated on dry base].

EXAMPLE 6

A 500 ml cylindrical reactor equipped with a mechanical stirrer, a thermometer, a reflux condenser and a dropping funnel, was charged with 3-pyridine acetic acid hydrochloride (6.94 g, 0.04 mole), phosphorous acid (9.84 g, 0.12 mole), ortho-phosphoric acid (11.80 g, 0.12 mole) and toluene (50 ml). The suspension was heated to 90° C. and phosphorous oxychloride (11.2 ml, 0.12 mole) was added dropwise during 20 minutes. The reaction mixture was then heated to 95° C. for 20.5 hours. Water (50 ml) was added after cooling the reaction mixture to 80° C. The mixture was stirred vigorously until the solidified product dissolved completely. The toluene and the aqueous phases were separated and the aqueous phase was heated at 95° C. for 5.5 hours. The aqueous phase was cooled to 25° C. and absolute ethanol (50 ml) was added to precipitate the final product. The suspension was cooled to 5° C. for 1 hour. The white product was filtered, washed with absolute ethanol (2×20 ml) and dried at 65° C. for 5 hours to obtain 7.70 g (68%) of risedronic acid monohydrate.

EXAMPLE 7

A 2L cylindrical reactor equipped with a mechanical stirrer, a thermometer, a reflux condenser and a dropping funnel, was charged with 3-pyridine acetic acid hydrochloride (27.7 g, 0.16 mole), phosphorous acid (39.4 g, 0.48 mole), ortho-phosphoric acid (47.2 g, 0.48 mole) and toluene (200 ml). The suspension was heated to 90° C. and phosphorous oxychloride (44.8 ml, 0.48 mole) was added dropwise during 20 minutes. The reaction mixture was then heated to 95° C. for 20.5 hours. Water (200 ml) was added after cooling the reaction mixture to 80° C. The mixture was stirred vigorously until the solidified product dissolved completely. The toluene and the aqueous phases were separated and the aqueous phase was heated at 95° C. for 5.5 hours. The aqueous phase was cooled to 25° C. and absolute ethanol (200 ml) was added to precipitate the final product. The suspension was cooled to 5° C. for 1 hour. The white product was filtered, washed with absolute ethanol (2×80 ml) and dried at 65° C. for 5 hours to obtain 38.2 g (84%) of risedronic acid monohydrate.

EXAMPLE 8

A 500 ml cylindrical reactor equipped with a mechanical stirrer, a thermometer, a reflux condenser and a dropping funnel, was charged with 3-pyridine acetic acid hydrochloride (6.94 g, 0.04 mole), phosphorous acid (9.84 g, 0.12 mole) and toluene (50 ml). The suspension was heated to 90° C. Hyfllo Super-Cel diatomaceous silica (17.50 g, 50% w/w of all the reagents) was added in portions after the mixture of 3-pyridyl acetic acid and $H_3PO_3$ was melted, to obtain an heterogeneous suspension. Phosphorous oxychloride (11.2 ml, 0.12 mole) was then added dropwise during 12 minutes. The reaction mixture was then heated to 95° C. for 3 hours. Water (75 ml) was added after cooling the reaction mixture to 65° C. The mixture was stirred vigorously for 30 minutes and then the Hyfllo was removed by filtration. The toluene and the aqueous phases were separated and the aqueous phase was heated at 95° C. for 16 hours. The aqueous phase was cooled to 25° C. and absolute ethanol (75 ml) was added to precipitate the final product. The suspension was cooled to 5° C. for 1 hour. The white product was filtered, washed with absolute ethanol (2×20 ml) and dried in a vacuum oven at 50° C. for 24 hours to obtain 6.30 g (56%) of risedronic acid monohydrate.

EXAMPLE 9

A 2L cylindrical reactor equipped with a mechanical stirrer, a thermometer, a reflux condenser and a dropping funnel, was charged with 3-pyridine acetic acid hydrochloride (27.7 g, 0.16 mole), phosphorous acid (39.4 g, 0.48 mole) and toluene (200 ml). The suspension was heated to 90° C. Hyfllo Super-Cel diatomaceous silica (70 g, 50% w/w of all the reagents) was added in portions after the mixture of 3-pyridyl acetic acid and $H_3PO_3$ was melted, to obtain an heterogeneous suspension. Phosphorous oxychloride (44.8 ml, 0.48 mole) was then added dropwise during 12 minutes. The reaction mixture was then heated to 95° C. for 3 hours. Water (300 ml) was added after cooling the reaction mixture to 65° C. The mixture was stirred vigorously for 30 minutes and then the Hyfllo was removed by filtration. The toluene and the aqueous phases were separated and the aqueous phase was heated at 95° C. for 16 hours. The aqueous phase was cooled to 25° C. and absolute ethanol (300 ml) was added to precipitate the final product. The suspension was cooled to 5° C. for 1 hour. The white product was filtered, washed with absolute ethanol (2×80 ml) and dried in a vacuum oven at 50° C. for 24 hours to obtain 31.7 g (71%) of risedronic acid monohytdrate.

EXAMPLE 10

A 250 ml cylindrical reactor equipped with a mechanical stirrer, a thermometer, a reflux condenser and a dropping funnel, was loaded with 3-pyridine acetic acid hydrochloride (6.94 g, 0.04 mole), phosphorous acid (9.84 g, 0.12 mole) and toluene (50 ml). The suspension was heated to 90° C. and phosphorous oxychloride (11.2 ml, 0.12 mole) was added dropwise during 20 minutes. The reaction mixture was then heated to 95° C. for 3.5 hours. Water (50 ml) was added after cooling the reaction mixture to 65° C. The mixture was stirred vigorously till the solidified product dissolved completely. The toluene and the aqueous phases were separated and the aqueous phase was heated at 95° C. for 16 hours. Then it was cooled to 5° C. during 3 hours and stirred at this temperature for an additional 40 hours. The white product was filtered, washed with water (2×25 ml) and dried in a vacuum oven at 50° C. for 24 hours to obtain 6.38 g (56%) of risedronic acid monohydrate.

EXAMPLE 11

A 250 ml cylindrical reactor equipped with a mechanical stirrer, a thermometer, a reflux condenser and a dropping funnel, was loaded with 4-amino butyric acid (GABA) (4.12 g, 0.04 mole), phosphorous acid (9.84 g, 0.12 mole) and toluene (50 ml). The suspension was heated to 85° C. and phosphorous oxychloride (11.2 ml, 0.12 mole) was added dropwise during 20 minutes. The reaction mixture was then heated to 95° C. for 2.5 hours. Water (50 ml) was added after cooling the reaction mixture to 65° C. The mixture was stirred vigorously till the solidified product dissolved completely. The toluene and the aqueous phases were separated and the aqueous phase was heated at 95° C. for 16 hours. The aqueous phase was cooled to 25° C. and absolute ethanol (100 ml) was added to precipitate the final product. The suspension was cooled to 5° C. for 1 hour. The white product was filtered, washed with absolute ethanol (2×50 ml) and dried in a vacuum oven at 50° C. for 20 hours to obtain 8.20 g (82%) of alendronic acid monohydtare.

EXAMPLE 12

A 500 ml cylindrical reactor equipped with a mechanical stirrer, a thermometer, a reflux condenser and a dropping funnel, was loaded with GABA (4.12 g, 0.04 mole), phosphorous acid (9.84 g, 0.12 mole), ortho-phosphoric acid (11.80 g, 0.12 mole), and toluene (50 ml). The suspension was heated to 90° C. and phosphorous oxychloride (11.2 ml, 0.12 mole) was added dropwise during 20 minutes. The reaction mixture was then heated to 95° C. for 20.5 hours. Water (50 ml) was added after cooling the reaction mixture to 80° C. The mixture was stirred vigorously till the solidified product dissolved completely. The toluene and the aqueous phases were separated and the aqueous phase was heated at 95° C. for 5.5 hours. The aqueous phase was cooled to 25° C. and absolute ethanol (50 ml) was added to precipitate the final product. The suspension was cooled to 5° C. for 1 hour. The white product was filtered, washed with absolute ethanol (2×20 ml) and dried at 65° C. for 5 hours to obtain 6.80 g (68%) of alendronic acid monohydtare.

EXAMPLE 13

A 500 ml cylindrical reactor equipped with a mechanical stirrer, a thermometer, a reflux condenser and a dropping funnel, was loaded with GABA (4.12 g, 0.04 mole), phosphorous acid (9.84 g, 0.12 mole) and toluene (50 ml). The suspension was heated to 90° C. Hyfllo Super-Cel diatomaceous silica (17.50 g, 50% w/w of all the reagents) was added in portions after the mixture of 3-pyridyl acetic acid HCL and $H_3PO_3$ was melted to obtain an heterogeneous suspension. Phosphorous oxychloride (11.2 ml, 0.12 mole) was then added dropwise during 12 minutes. The reaction mixture was then heated to 95° C. for 3 hours. Water (75 ml) was added after cooling the reaction mixture to 65° C. The mixture was stirred vigorously for 30 minutes and then the Hyfllo was removed by filtration. The toluene and the aqueous phases were separated and the aqueous phase was heated at 95° C. for 16 hours. The aqueous phase was cooled to 25° C. and absolute ethanol (75 ml) was added to precipitate the final product. The suspension was cooled to 5° C. for 1 hour. The white product was filtered, washed with absolute ethanol (2×20 ml) and dried in a vacuum oven at 50° C. for 24 hours to obtain 5.60 g (56%) of alendronic acid monohydrate.

EXAMPLE 13

Preparation of Zaledronic Acid Monohydrate (ZLD-Ac)

Six experiments were run reacting imidazoleacetic acid (IAA), hosphorous acid ($H_3PO_3$) and hosphorous oxychloride ($POCl_3$) according to the following the general procedure. The specific conditions of each experiment, and the results obtained, are given in Table I.

A cylindrical reactor equipped with a mechanical stirrer, a thermometer, a reflux condenser and a dropping funnel, is loaded with 1-midazoleacetic acid (IAA), phosphorous acid and a diluent (silicon oil). The obtained suspension is heated to 75° C.–80° C. and phosphorous oxychloride is added drop-wise. The reaction mixture is then heated to 75° C.–100° C. for 1–34 hours. Water is added at 80° C.–100° C. The resulting mixture is stirred vigorously for about 15 minutes. [N.b. in some cases, when silicon oil is used as a diluent, there is a need to add toluene in order to improve the separation between the oily phase and the aqueous phase]. Then the phases are separated. The aqueous phase is put in a clean reactor and heated to 95° C.–100° C. for 13.5–19 hours. The aqueous phase is then cooled to 5° C. and absolute ethanol is added to obtain a precipitate after stirring at 5° C. for 2.5–4 hours. The white product is then filtered, washed with absolute ethanol and dried in a vacuum oven at 50° C. for 17–24 hours to obtain zoledronic acid.

After recrystallization form water (26 volumes), zoledronic acid monohydrate is obtained (LOD by TGA=6.3%–9.3%).

TABLE 1

Preparation of ZLD-Ac Monohydrate starting from IAA, $H_3PO_3$ and $POCl_3$

| Example | Raw material (grams of IAA) | Ratio of reactants (equivalents) IAA/ $H_3PO_3$/ $POCl_3$ | Diluent/ volumes per grams of IAA | Temp of reaction | Temp of reaction | Amount of water of the hydrolysis step | Addition of Toluene to improve phases separation | Time of hydrolysis step | Amount of abs.EtOH/ Acetone for the precipitation of ZLD-Ac | LOD by TGA | Yield (grams of ZLD-Ac) |
|---|---|---|---|---|---|---|---|---|---|---|---|
| 1 | IAA · HCl (5.4 g) | 1/3.6/4.5 | Silicon oil/ 6.5 vol. | 80° C. | 24 hrs | 45 ml | 50 ml | 19 hrs | 90 ml(EtOH) | 9.1% | 79% (7.8 g) |
| 4 | IAA · HCl (4.9 g) | 1/3/3.75 | Silicon oil/ 5.5 vol. | 80° C. | 22 hrs | 54 ml | 54 ml | 19 hrs | 54 ml(EtOH) | 6.8% | 76% (6.7 g) |
| 6 | IAA · HCl (5.9 g) | 1/2/3 | Silicon oil/ 5.5 vol. | 80° C. | 23 hrs | 33 ml | — | 16 hrs | 200 ml(EtOH) | 7.9% | 38% (4.0 g) |
| 7 | IAA · HCl (6.0 g) | 1/4/4 | Silicon oil/ 5.5 vol. | 80° C. | 11 hrs | 33 ml | 33 ml | 16 hrs | 33 ml(EtOH) | 9.3% | 74% (8.2 g) |
| 8 | IAA (12.0 g) | 1/3/3.75 | Silicon oil/ 6.0 vol. | 80° C. | 17 hrs | 72 ml | — | 16 hrs | — | 7.7% | 72% (20.0 g) |
| 9 | IAA (70 g) | 1/3/3.75 | Silicon oil/ 7.0 vol. | 80° C. | 34 hrs | 490 ml | 490 ml | 16 hrs | 490 ml(EtOH) (addition of EtOH at reflux temp.) | 6.3% | 59% (95.1 g) Purity by HPLC 98.3%* |

*HPLC method:
Column: Phenomenex Phenyl-Hexyl 5 um, 250 × 4.6 mm
Mobile phase: 40 mM Octansulfonic acid sodium salt in 1% $HClO_4$, 0.2% $H_3PO_4$:Methanol (85:15)
Detection: 220 nm

We claim:

1. A method of making a bisphosphonic acid comprising the step of combining a carboxylic acid, phosphorous acid, and a halophosporous compound selected from $PCl_3$, $PCl_5$, $POCl_3$, $PBr_3$, $POBr_3$, and $PBr_5$ in the presence of a diluent that is either an aromatic hydrocarbon in combination with a codiluent that is ortho-phosphoric acid, or a silicone fluid,-wherein, when the diluent includes an aromatic hydrocarbon, a polyalkylene glycol is not present as a codiluent in the reaction mixture.

2. The method of claim 1 wherein the phosphorous acid and the halophosphorous compound are each combined together in at least a first portion and a second portion.

3. The method of claim 1 wherein the diluent is an aromatic hydrocarbon in combination with a codiluent that is ortho-phosphoric acid and the reaction is conducted in the presence of a heterogeneous solid support.

4. The method of claim 3 wherein the heterogeneous solid support is diatomite silica.

5. The method of claim 3 wherein the aromatic hydrocarbon is toluene.

6. The method of claim 1 wherein the silicone fluid is a poly(dimethysiloxane).

7. The method of claim 1 wherein the halophosphorous compound is $POCl_3$.

8. The method of claim 1 wherein the carboxylic acid is selected from the group consisting of 4-aminobutanoic acid, (3-pyridyl)ethanoic acid, (1-imidazoyl)ethanoic acid, N-(n-pentyl)-N-methyl-3-aminopropanoic acid, 2(imidazo[1,2-a]pyridin-3-yl)ethanoic acid, and 6-aminohexanoic acid, and the hydrochlorides thereof.

9. The method of claim 1 further comprising the steps of:
combining the reaction mixture with water or a water solution of a non-oxidizing acid, whereby at least aqueous and non-aqueous phases are formed,
separating the aqueous phase,
combining the aqueous phase with ethanol, whereby a precipitate is formed, and
isolating the bisphosphonic acid.

10. The method of claim 9 wherein the carboxylic acid is 3-aminobutanoic acid or its hydrochloride and the isolated bisphosphonic acid is alendronic acid monohydrate.

11. The method of claim 9 wherein the carboxylic acid is (3-pyridyl)ethanoic acid or its hydrochloride and the isolated bisphosphonic acid is risedronic acid monohydrate.

12. A method of making alendronic acid monohydrate comprising the steps of:
a) combining 4-aminobutanoic acid, phosphorous acid, and a halophosporous compound selected from $PCl_3$, $PCl_5$, $POCl_3$, $PBr_3$, $POBr_3$, and $PBr_5$ at a temperature of about 80° C. to about 100° C. in the presence of a diluent that is either an aromatic hydrocarbon in combination with ortho-phosphoric acid, or a silicone fluid to form a reaction mixture, wherein, when the diluent is an aromatic hydrocarbon, a polyalkylene glycol is not present as a codiluent in the reaction mixture,
b) combining the reaction mixture with water, whereby an aqueous and a non-aqueous phase are formed,
c) separating the aqueous phase,
d) combining the aqueous phase with ethanol whereby a suspension comprising alendronic acid is formed, and
e) isolating alendronic acid monohydrate from the suspension.

13. The method of claim 12 wherein the diluent is an aromatic hydrocarbon in combination with ortho-phosphoric acid and a heterogeneous solid support is combined in the reaction mixture and wherein the method further comprises the step of filtering the aqueous and non-aqueous phases before the aqueous phase is separated.

14. A method of making risedronic acid monohydrate comprising the steps of:
a) combining (3-pyridyl)ethanoic acid or its hydrochloride salt, phosphorous acid, and a halophosporous compound selected from $PCl_3$, $PCl_5$, $POCl_3$, $PBr_3$, $POBr_3$, and $PBr_5$ at a temperature of about 80° C. to about 100° C. in the presence of a diluent that is an aromatic hydrocarbon or a silicone fluid to form a reaction mixture, with the proviso that, when the diluent is an aromatic hydrocarbon, a polyalkylene glycol is not present as a codiluent in the reaction mixture,
b) combining the reaction mixture with water, whereby an aqueous and a non-aqueous phase are formed,
c) separating the aqueous phase,
d) combining the aqueous phase with ethanol whereby a suspension comprising risedronic acid is formed, and
e) isolating risedronic acid monohydrate from the suspension.

15. The method of claim 14 wherein, when the diluent is an aromatic hydrocarbon, ortho-phosphoric acid codiluent is combined in the reaction mixture.

16. The method of claim 14 wherein the diluent is an aromatic hydrocarbon and a heterogeneous solid support is combined in the reaction mixture and wherein the method further comprises the step of filtering the aqueous and non-aqueous phases before the aqueous phase is separated.

* * * * *

UNITED STATES PATENT AND TRADEMARK OFFICE
CERTIFICATE OF CORRECTION

PATENT NO.        : 7,038,083 B2
APPLICATION NO.   : 10/442001
DATED             : May 2, 2006
INVENTOR(S)       : Lidor-Hadas et al.

It is certified that error appears in the above-identified patent and that said Letters Patent is hereby corrected as shown below:

Title page, Item [75], Line 1
Change the inventor's name from "Rami Lidor-Hadas" to
-- Ramy Lidor-Hadas --

Signed and Sealed this

Twenty-first Day of July, 2009

JOHN DOLL
*Acting Director of the United States Patent and Trademark Office*